United States Patent [19]

Ertürk et al.

[11] Patent Number: 5,460,052

[45] Date of Patent: Oct. 24, 1995

[54] APPARATUS AND METHOD FOR MEASURING COMPOSITE INTERFACE PROPERTIES

[75] Inventors: Turgay Ertürk, Lowell; William Chepolis, Bedford, both of Mass.

[73] Assignee: University of Massachusetts Lowell, Lowell, Mass.

[21] Appl. No.: 281,793

[22] Filed: Jul. 28, 1994

[51] Int. Cl.$^6$ .................................................. G01N 3/22
[52] U.S. Cl. ............................. 73/847; 73/814; 73/843; 73/854
[58] Field of Search .......................... 73/814, 847, 854, 73/856, 860, 788, 794, 783, 843

[56] References Cited

U.S. PATENT DOCUMENTS

| | | | |
|---|---|---|---|
| 2,784,587 | 3/1957 | Harvey et al. | 73/847 |
| 3,661,012 | 5/1972 | Yamazaki et al. | 73/814 |
| 3,754,437 | 8/1973 | Kanbel et al. | 73/814 |
| 4,110,829 | 8/1978 | Boys | 73/847 |
| 4,476,727 | 10/1984 | Hawk et al. | 73/847 |
| 4,566,335 | 1/1986 | Singhal | 73/856 |
| 4,958,522 | 9/1990 | Mckinlay | 73/847 |

FOREIGN PATENT DOCUMENTS

| | | | |
|---|---|---|---|
| 0805105 | 2/1981 | U.S.S.R. | 73/814 |
| 0836692 | 6/1981 | U.S.S.R. | 73/814 |

OTHER PUBLICATIONS

Cook, R. F., et al., "Stick–Slip During Fibre Pull–Out," *Scripta Metallurgica*, 23:1725–1730 (1989).

Hsueh, C. H., "Evaluation of Interfacial Shear Strength, Residual Clamping Stress and Coefficient of Friction for Fiber–Reinforced Ceramic Composites," *Acta Metall. Mater.*, 38:403–409 (1990).

Marshall, D. B., "Analysis of Fiber Debonding and Sliding Experiments in Brittle Matrix Composites," *Acta Metall. Mater.*, 40:427–441 (1992).

Greszczuk, L. B., "Theoretical Studies of the Mechanics of the Fiber–Matrix Interface in Composites," *Interfaces in Composites*, ASTM STP 452, American Soc. for Testing and Materials, pp. 42–58 (1969).

Stang, H., et al., "Pullout Problem: Stress Versus Fracture Mechanical Approach," *J. Engin. Mechanics*, 116:2136–2150 (1990).

Marshall, D. B., et al., "Measurement of Interfacial Debonding and Sliding Resistance in Fiber Reinforced Intermetallics," *Acta Metall. Mater.*, 40:443–454 (1992).

Bright, J. D., et al., "Interfacial Bonding and Friction in Silicon Carbide (Filament)–Reinforced Ceramic– and Glass–Matrix Composites," *J. Am. Ceram. Soc.*, 72:1891–1898 (1989).

Aveston, J., et al., "PAPER 2—Single and Multiple Fracture," *The Properties of Fiber Composites*, Conference Proceedings, National Physical Laboratory, Guildford IPC Science and Tech. Press, Surrey, England, pp. 15–26 (1971).

Fuller, E. R., et al., "Determination of Fiber–Matrix Interfacial Properties of Importance to Ceramic Composite Toughening," Proceedings of NATO Advanced Workshop on Toughening Mechanisms, pp. 1–19 (1991).

(List continued on next page.)

*Primary Examiner*—Richard Chilcot
*Assistant Examiner*—George M. Dombroski
*Attorney, Agent, or Firm*—Hamilton, Brook, Smith & Reynolds

[57] ABSTRACT

An apparatus and method for measuring interface properties of a composite test specimen includes a first jaw for gripping the specimen. The specimen has a fiber extending through a matrix forming a fiber-matrix interface with a portion of the fiber extending from the matrix. A second jaw grips the fiber extending from the matrix. A motor drive coupled to the first jaw rotates the fiber relative to the matrix. The torque transmitted through the fiber-matrix interface to the fiber is measured with a stationary torque transducer coupled to the second jaw with respect to the angular rotation of the fiber relative to the matrix. From the resulting torque-twist angle plot, composite interface properties such as interfacial fracture energy and frictional traction can be obtained.

22 Claims, 4 Drawing Sheets

OTHER PUBLICATIONS

Brun, M. K., "Measurement of Fiber/Matrix Interfacial Shear Stress at Elevated Temperatures," *J. Am. Ceram. Soc.*, 75:1914–1917 (1992).

Marshall, D. B., "An Indentation Method for Measuring Matrix–Fiber Frictional Stresses in Ceramic Composites," Communications of the American Ceramic Soc., pp. C–259–C–260 (1984).

Griffin, C. W., "Evaluation of Interfacial Properties in Borosilicate–SiC Composites Using Pullout Tests," *Ceram. Eng. Sci. Proc.*, 9:671–678 (1988).

Takaku, A., et al., "The Effect of Interfacial Radial and Shear Stress on Fibre Pull–Out in Composite Materials," *J. Phys. D: Appl. Phys.*, 6:2038–2047 (1973).

Thouless, M. D., and Evans, A. G., "Effects of Pull–Out on the Mechanical Properties of Ceramic–Matrix Composites," *Acta Metall.*, 36:517–522 (1988).

Kerans, R. J., "Theoretical Analysis of the Fiber Pullout and Pushout Tests," *J. Am. Ceram. Soc.*, 74:1585–1596 (1991).

Charalambides, P. G., and Evans, A. G., "Debonding Properties of Residually Stressed Brittle–Matrix Composites," *J. Am. Ceram. Soc.*, 72:746–753 (1989).

Jero, P. D., and Kerans, R. J., "The Contribution of Interfacial Roughness to Sliding Friction of Ceramic Fibers in a Glass Matrix," *Scripta Metallurgica*, 24:2315–2318 (1990).

Parthasarathy, T. A., et al., "Extraction of Interface Properties from a Fiber Push–Out Test," *Scripta Metallurgica*, 25:2457–2462 (1991).

Eldridge, J. I., "Investigation of Interfacial Shear Strength in a SiC Fibre/Ti–24A1–11Nb Composite by a Fibre Push–Out Technique," *J. Materials Sci. Letters*, 8:1451–1454 (1989).

Atkinson, C., et al., "The Rod Pull Out Problem, Theory and Experiment," *J. Mech. Phys. Solids*, 30:97–120 (1982).

APPARATUS AND METHOD FOR MEASURING COMPOSITE INTERFACE PROPERTIES

BACKGROUND

Composite materials typically consist of a matrix in which high strength and modulus fibers are embedded for added modulus, strength or toughness. The fiber-matrix interface in composite materials plays a central role in determining the performance of a given composite, especially in metal and ceramic matrix composites. The strength and toughness of a composite material is influenced by the strength and fracture energy of the bond between the fiber and the matrix as well as the friction between the fiber and matrix once the bond is broken. The magnitude of the friction force between the fiber and the matrix is dependent upon the residual clamping stresses (compressive stresses) exerted on the fiber by the surrounding matrix, the coefficient of friction between the fiber and the matrix, and the area over which the fiber is in contact with matrix.

Currently, the interface properties of composite materials is typically determined by conducting tests on single fiber composite test specimens. One common single fiber composite interface test technique is the fiber pullout test in which a single fiber of a composite test specimen is pulled axially from the surrounding matrix. The force required to debond the fiber from the matrix as well as the force required to displace the fiber relative to the matrix after debonding is measured. Data from this test is difficult to interpret due to non-linear variations of stress, strain and frictional tractions along the embedded fiber length. These non-linear stress and strain variations arise primarily from a narrowing of the diameter of the fiber along its length caused by the lateral contraction of the fiber and which is otherwise known as Poisson's ratio effect. This results in variable compression forces exerted by the matrix on the fiber along the length of the embedded fiber which in turn causes variations of frictional force along the fiber-matrix interface. As a result, it is difficult to assign a simple frictional traction value to the fiber-matrix interface.

Another common single fiber test technique is the fiber pushout test which is similar to the fiber pullout test except that a fiber of the composite is pushed axially into the matrix. Data from this test is also difficult to interpret due to Poisson's ratio effect which, in this case, causes the diameter of the fiber to expand rather than contract. In addition, the data in the pushout test is also influenced by edge effects. Typically, edge effects are caused by defects such as cracks in the matrix, fiber or interface at both ends of the test specimen which weaken the interface. Edge effects are more dominant in the pushout test than the pullout test because a short specimen length is required for conducting the pushout test. Edge effects in short specimens represent a high percentage of the matrix along the embedded fiber length and as a result, further distorts fiber-matrix interface data in pushout test specimens. Pushout and pullout tests on identical specimens render dramatically different results, presumably due to the Poisson effect influencing respective test data in opposite ways.

SUMMARY OF THE INVENTION

Accordingly, there is a continuing need for a composite material test which can accurately measure interface properties of composite materials without being affected by Poisson's effects or edge effects.

The present invention provides an apparatus and method for measuring the interface properties of a specimen of composite material. A first jaw grips the specimen. The specimen has a fiber extending through a matrix forming a fiber-matrix interface with a portion of the fiber extending from the matrix. A second jaw grips the fiber extending from the matrix. A motor drive coupled to one jaw rotates the fiber relative to the matrix. A stationary torque transducer coupled to the other jaw measures the torque transmitted through the fiber-matrix interface with respect to the angular rotation of the fiber relative to the matrix.

In the preferred embodiment, the first jaw is coupled to the motor drive for rotating the specimen and the second jaw is coupled to the torque transducer for measuring torque transmitted through the fiber-matrix interface to the fiber. The motor drive is coupled to a three-axis slide adjustment for adjusting the position of the motor drive. The motor drive includes a stepper motor which is coupled to a gear reducer. The stepper motor is controlled by a controller which drives the stepper motor with electrical pulses. The angular rotation of the fiber relative to the matrix is determined by counting the number of electrical pulses used in driving the stepper motor, correlating the number of electrical pulses into angular rotation of the stepper motor and correlating the angular rotation of the stepper motor into angular rotation of the fiber relative to the matrix by accounting for the reduction ratio of the gear reducer.

An acoustic transducer bonded to the specimen is included for sensing acoustic emission or report from the specimen caused by the fiber debonding from the matrix during rotation. In response to the sensed acoustic report, the acoustic transducer produces a signal for signaling measurement of the torque transmitted through the fiber-matrix interface at the moment of the acoustic report.

The present invention provides an apparatus and method for accurately testing the interface properties of composite materials in which Poisson contraction or expansion effects are eliminated, edge effects are minimized and friction forces are constant. As a result, the present invention provides more accurate test results than previously obtainable with prior test techniques.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENT

Figure 1:
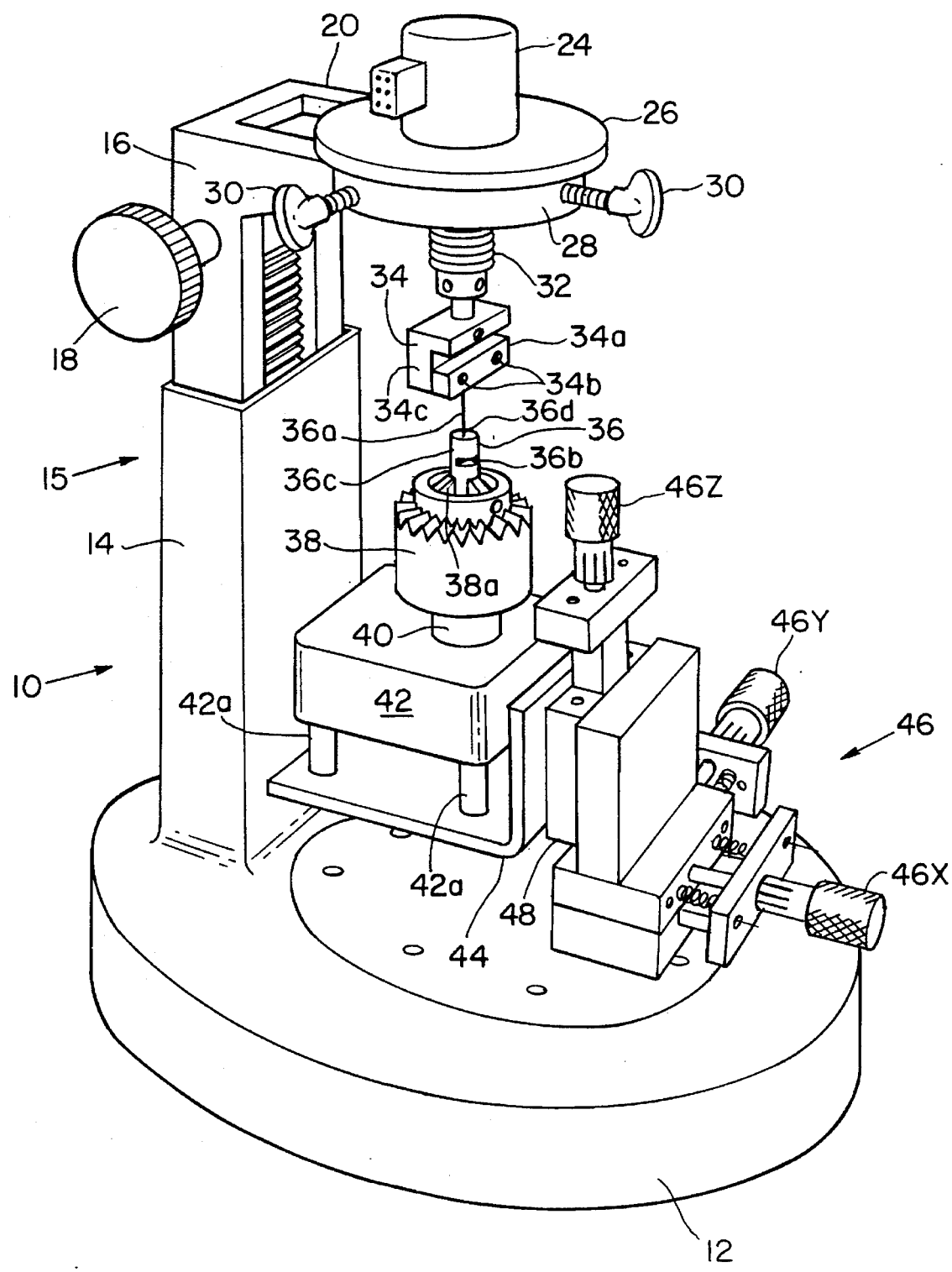
FIG. 1 is a perspective view of the present invention fiber twist test apparatus.
Figure 2:
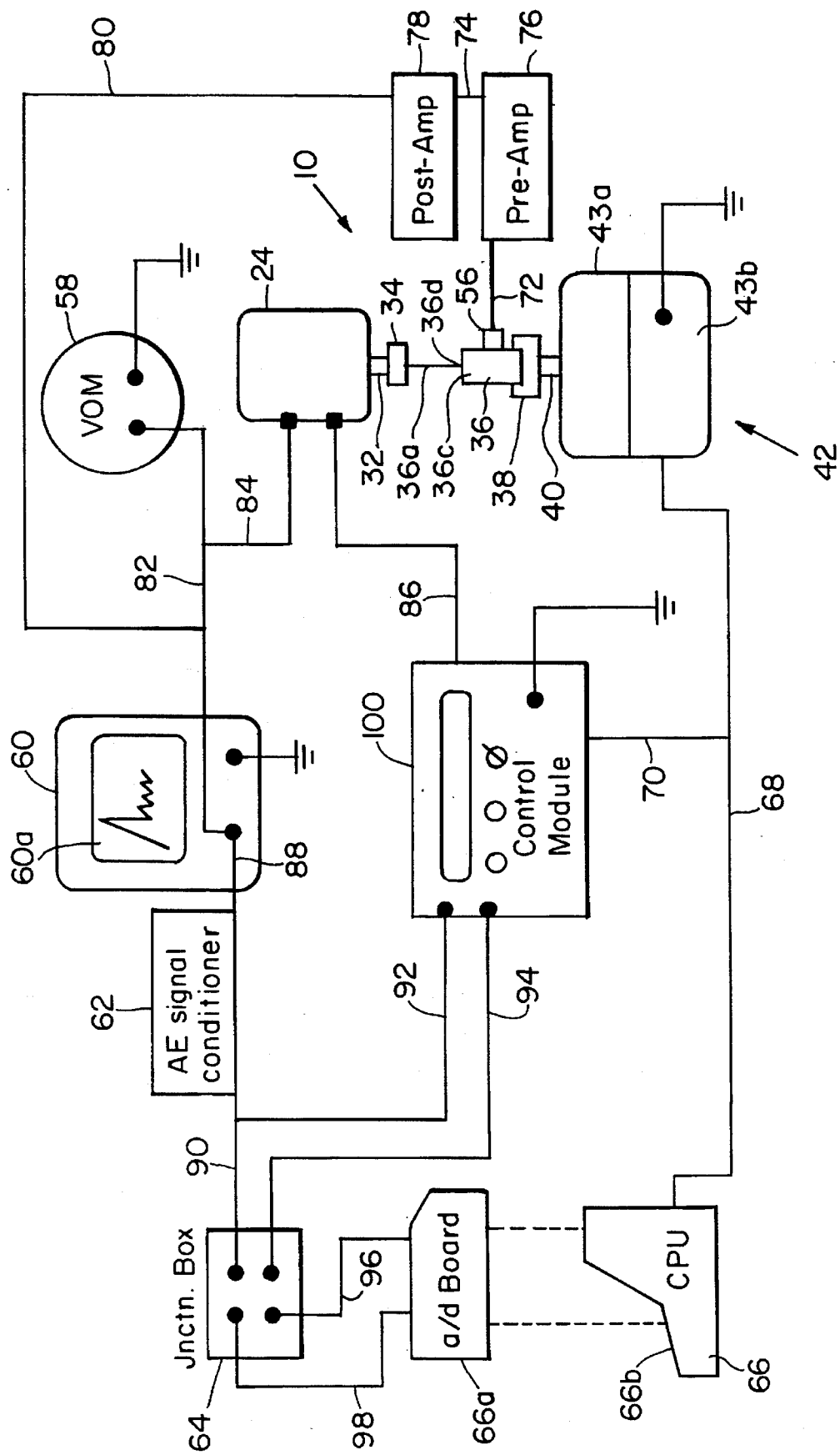
FIG. 2 is a schematic view of the control system for controlling the present invention fiber twist test apparatus.

Referring to FIGS. 1 and 2, fiber twist test apparatus 10 includes a base 12 to which a motor drive 42 is adjustably mounted by a three-axis slide adjustment 46. The motor drive 42 consists of a stepper motor 43b and a gear reducer 43a which is coupled to a rotatable chuck 38 by a drive shaft 40. Chuck 38 is capable of gripping and rotating test specimen 36. Extending upwardly from base 12 is an adjustable vertical column 15 to which torque transducer 24 is secured. A vice 34 is coupled to torque transducer 24 by a flexible coupling 32. Vice 34 grips fiber 36a extending from the matrix 36c of test specimen 36 for preventing rotation of fiber 36a.

The rotational speed, acceleration and deceleration of stepper motor 43b is controlled by computer 66 via control module 100. Control module 100 acts as a buffer for stepper motor commands from computer 66 and provides power to torque transducer 24 and stepper motor 43b. An acoustic transducer 56 is attached to test specimen 36 for detecting any acoustic energy released in association with debonding or sudden movement of the fiber 36a relative to its surrounding matrix 36c. A digital volt-ohmmeter 58 and digitizing oscilloscope 60 are electrically connected to acoustic transducer 56 and are connected in parallel with the voltage output of the torque transducer 24 for visually monitoring torque changes during tests as well as capturing acoustic energy signatures generated by test specimen 36. A data acquisition board 66a within computer 66 for receiving and processing test data is electrically connected to control module 100, oscilloscope 60, volt-ohmmeter 58, torque transducer 24 and acoustic transducer 56 via junction box 64. Computer 66 includes a keyboard 66b for entering test parameters.

In operation, test specimen 36 is tested by rotating specimen 36 with motor drive 42 for a predetermined angle of rotation. The rotation angle can vary depending upon the materials of the test specimen with rotation angles between 45° and 360° being typical. Since fiber 36a is held stationary by vice 34, matrix 36c is rotated relative to fiber 36a, thereby twisting fiber 36a.

The command for the rotational angle and other motor parameters such as motor speed, steps per pulse and acceleration is first downloaded from computer 66 into control module 100 via lines 68 and 70. Control module 100 then provides the commands to stepper motor 43b via lines 70 and 68 in a series of electrical pulses. Each pulse rotates stepper motor 43b a known amount. For example, 160 electrical pulses can be required for one degree of rotation of stepper motor 43b. The electrical pulse data is also provided by control module 100 to data acquisition board 66a via line 94, junction box 64 and line 96. The rotation of stepper motor 42 is reduced by gear reducer 43a which, for example, can have a 144-to-1 reduction. As a result, the degree of rotation of specimen 36 can be determined by computer 66 by counting the number of electrical pulses used in driving stepper motor 43b, correlating the electrical pulses into the angular rotation of stepper motor 43b, and accounting for the reduction ratio of gear reducer 43a.

As specimen 36 rotates, torque transducer 24 measures the torque transferred through the fiber-matrix interface 36d to fiber 36a at intervals coinciding with each electrical pulse that is delivered to stepper motor 43b. The power to torque transducer 24 is provided by control module 100 via line 86. Torque transducer 24 produces a voltage which is proportional to the torque sensed. This voltage is provided to data acquisition board 66a via lines 84, 82, 88 and 90, junction box 64 and line 98. Accordingly, the sensed torque is recorded with respect to angular rotation of stepper motor 43b.

Rotating matrix 36c relative to fiber 36a eventually debonds fiber 36a from matrix 36c. When the fiber 36a debonds or suddenly rotates within matrix 36c, an acoustic energy report results. Acoustic transducer 56 senses this acoustic report and provides a signal. This signal is a single DC square wave which lasts until the next electrical pulse is provided to stepper motor 43b. As a result, the signal lasts for a duration that spans at least for the time between electrical pulses or one data collection event. The signal from acoustic transducer 56 is provided to a pre-amp 76 and post amp 78 via lines 72 and 74 for amplification. The signal then passes to acoustic energy signal conditioner 62 via lines 80, 82 and 88. The signal is then transformed into a longer pulse by the acoustic energy signal conditioner 62 which is provided to control module 100 via line 92 for commanding the torque to be measured by torque transducer 24 which can be at moments between electrical pulses.

Once the fiber 36a has debonded from matrix 36d, fiber 36a rotates within matrix 36d. The torque required to overcome frictional forces to rotate fiber 36a within 36d is then measured until stepper motor 43b stops rotating. The torque is measured with respect to angular rotation of test specimen 36 and can be viewed on screen 60a of oscilloscope 60 or printed out on a printer.

Figure 3:
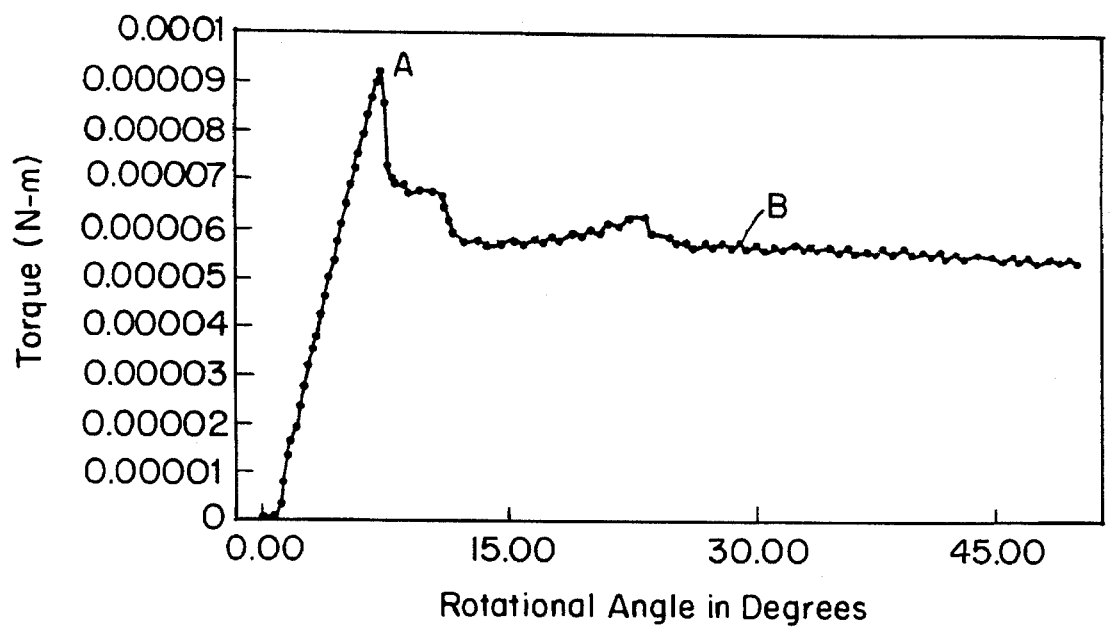
FIG. 3 is a graph showing the torque transmitted through the fiber-matrix interface of a test sample with respect to rotation angle.

An example of torque data versus angular rotation is depicted in FIG. 3. Point "A" on the graph represents the torque required to debond the fiber 36a from matrix 36c. The near horizontal line "B" after the 15° rotational angle represents the torque required to overcome friction between the fiber 36a and the matrix 36c as the fiber 36a rotates within matrix 36c.

Once the test data is obtained, fiber-matrix interface properties can be determined. One such property is residual stress. Residual stress is caused by the coefficient of thermal expansion difference between a fiber and a matrix. The expression for residual stress at the fiber-matrix interface of a test specimen can be stated in terms of a rod (fiber) surrounded by a thick walled cylinder (matrix). The stress buildup is assumed to occur during temperature reduction from the stress relief point to the ambient temperature prevailing during testing.

The thick walled cylinder is assumed to have a wall thickness of at least ten times the diameter of the embedded fiber. Variations greater than this ratio affect residual stress calculations by less than one percent, for example, when compared to a wall to fiber dimension ratio of fifteen. This stress is indicated as interference or shrink fit pressure (P) for thick walled cylinders in the following expression:

$$P := \frac{\delta}{R_f \cdot \left[ \frac{1}{E_f} \cdot \left[ \frac{(R_m)^2 + (R_f)^2}{(R_m)^2 - (R_m)^2} + v_m \right] + \frac{1 - v_f}{E_f} \right]} \quad \text{Eq. 1}$$

where:

$\delta$ = the interference dimension at ambient temperature between the fiber and matrix $R_f$ = the outside diameter of the fiber
$R_m$ = the outside diameter of the matrix
$E_f$ = the elastic modulus of the fiber
$\nu_f$ = the Poisson ratio of the fiber and
$\nu_m$ = the Poisson ratio of the matrix.

Another fiber-matrix interface property which can be determined is debonding stress. The torque required to debond a fiber from a matrix is given by:

$$T = Fr \qquad \text{Eq. 2}$$

where:
F = the applied force
r = radius of the fiber

By rearranging Equation 2, the force required to debond a fiber from a matrix can be found:

$$F = T/r \qquad \text{Eq. 3}$$

The debonding stress required for initiating movement between the fiber 36a and the matrix 36c can then be found by:

$$\tau = F/A \qquad \text{Eq. 4}$$

where:
A = the stressed area

Still another fiber-matrix interface property which can be determined is the stress for overcoming frictional traction. The stress to overcome frictional traction after debonding can be expressed in terms of the friction force required to move the debonded fiber relative to the surrounding matrix. This friction force can be defined as:

$$F_f = T/r \qquad \text{Eq. 5}$$

According to the theory of Coloumbic friction, $$F_f = N \times \text{area} \times \mu \qquad \text{Eq. 6}$$

where:
N = the normal force which equates to the residual stress normal to the interface caused by the fiber-matrix coefficient of thermal expansion difference otherwise referred to as the residual clamping stress P; and $\mu$ = the coefficient of friction between the fiber and matrix.

Accordingly, the stress for overcoming the friction traction after debonding is given as:

$$\tau = F_f/A \qquad \text{Eq. 7}$$

When a single-event catastrophic debond does not occur during testing, measurements of fracture energy of the fiber-matrix interface 36d requires knowledge of the incremental propagated crack length. In fiber twist tests, the slope of the torque-twist angle curve depends on the free length of fiber 36a between the vice 34 and the matrix 36c plus the debonded length. In situations of incomplete debonding, the stressed fiber 36a does not return to its original position upon the removal of load, but retains some displacement due to friction.

Figure 4:
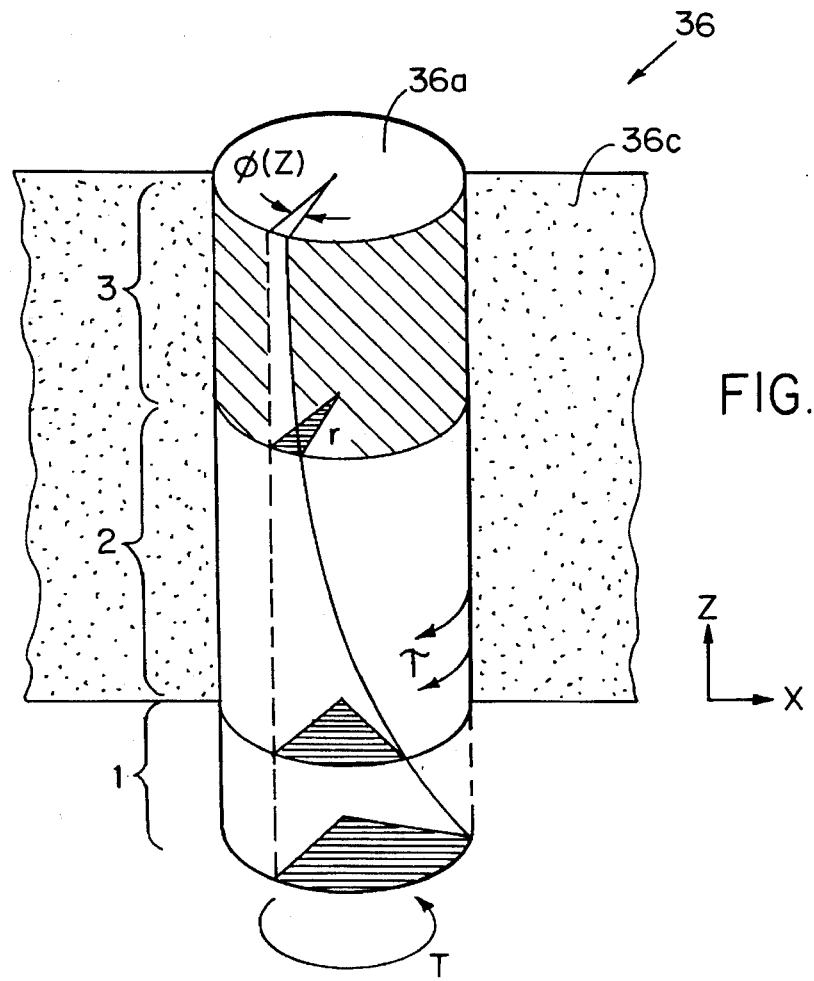
FIG. 4 is a schematic representation of a fiber embedded in matrix subjected to torque.

FIG. 4 depicts a situation in which there is incomplete debonding. In region 1, fiber 36a is unembedded in matrix 36c. In region 2, fiber 36a is debonded from matrix 36c while in region 3, fiber 36a remains bonded to matrix 36c.

The torque required for twisting a fiber at any given depth within a matrix in a situation of incomplete debonding is given by:

$$T(z) = \tau 2\pi r^2 z \qquad \text{Eq. 8}$$

where:
z = the depth into the test specimen
The shear stress is given by:

$$\tau = \frac{1}{2\pi r^2} \frac{dT}{dz} \qquad \text{Eq. 9}$$

The retained twist angle of the fiber can be found by:

$$\phi = \frac{\tau \pi r^2 z^2}{G I_p} \qquad \text{Eq. 10}$$

where:
G = the shear modulus of elasticity of the fiber
$I_p$ = the polar moment of inertia of the fiber The fiber twist test apparatus 10 is described below in more detail. Motor drive 42 is mounted to three-axis slide adjustment 46 by spacers 42a and L bracket 44. L bracket 44 is mounted to mounting plate 48 of three-axis slide adjustment 46. The three-axis slide adjustment 46 has knobs 46x, 46y and 46z for adjusting the position of motor drive 42 in the x, y and z axes respectively. Chuck 38 is similar to those chucks used on drill presses and lathes and includes three adjustable jaws 38a for gripping specimen 36. The rotational angle of test specimen 36 is measurable to within 0.00625° and the rotational speed can be as low as 1° per second.

Adjustable column 15 includes a rigid hollow member 14 extending vertically from base 12 and a moveable member 16 having an adjustment knob 18 for adjusting the height of member 16 relative to hollow member 14. Extending perpendicularly from moveable member 16 is a horizontal arm 20. Torque transducer 24 is mounted within a bore in arm 20. The bore has a larger diameter than the diameter of torque transducer 24. A plate 26 mounted to torque transducer 24 provides vertical support for torque transducer 24 and thumb screws 30 provide adjustment of torque transducer 24 in the horizontal plane. Alternatively, torque transducer 24 can be mounted to arm 20 without any means of adjustment. Additionally, three-axis slide adjustment 46 and adjusting column 15 can be substituted for non-adjustable members.

Torque transducer 24 has a precisely machined and calibrated internal torque shaft. The shaft angle of twist is indicated by an output DC voltage that varies linearly with the angle of twist. In the preferred embodiment, the output voltage is generated by a photo-diode circuit that reads a calibrated light source. Output voltage is controlled by two slotted disks that change "aperture" size in proportion to torque experienced by the calibrated shaft. The torque range of the shaft is well within the linear range of its stress-strain relationship. The input shaft of the transducer is "hung" vertically to avoid side loading from its guide bearing. Applied torque is measurable to within one percent of the maximum transducer range, $7.05 \times 10^{-4}$ N.m (0.1 in. –02).

Figure 5:
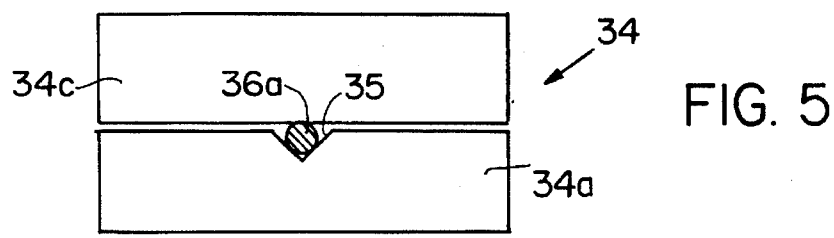
FIG. 5 is a bottom view of the vice for gripping the fiber.

The vice 34 is coaxially coupled to the transducer shaft via flexible coupling 32 which has a high torsional, but low axial stiffness. The low axial stiffness compensates for inadvertent angular or lateral misalignment between the transducer shaft and fiber 36a, and to minimize inadvertent tension or compression in the torsional load train. Vice 34 includes a stationary jaw 34c and a moveable jaw 34a which is mounted to stationary jaw 34c by screws 34b. As seen in FIG. 5, moveable jaw 34a includes a vee-shaped groove 35 for capturing fiber 36a which can be of the order of 140 μm in diameter.

Figure 6:
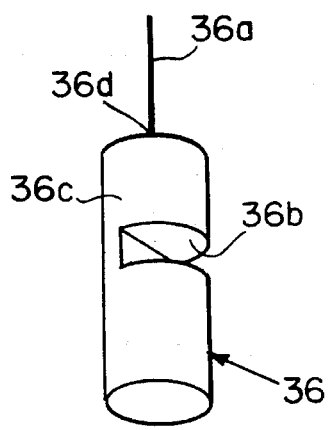
FIG. 6 is a perspective view of the composite material test specimen.

FIG. 6 depicts test specimen 36 in greater detail. In order to obtain test data with some consistency, the length of the fiber-matrix interface 36d must be controlled. As a result, a cut 36b is made into specimen 36 with a cutting wheel to cut through fiber 36a.

Figure 7:
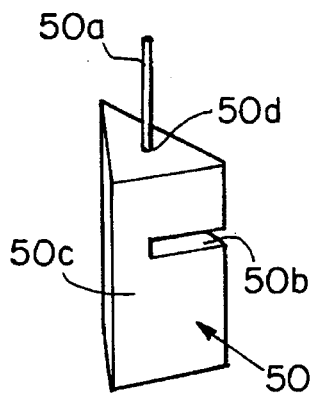
FIG. 7 is a perspective view of another preferred composite material test specimen.

FIG. 7 depicts a triangular test specimen 50 which has a fiber 50a within a matrix 50c forming a fiber-matrix interface 50d. A cut 50b in matrix 50c controls the length of the fiber-matrix interface 50d. Specimen 50 can be substituted for specimen 36.

Figure 8:
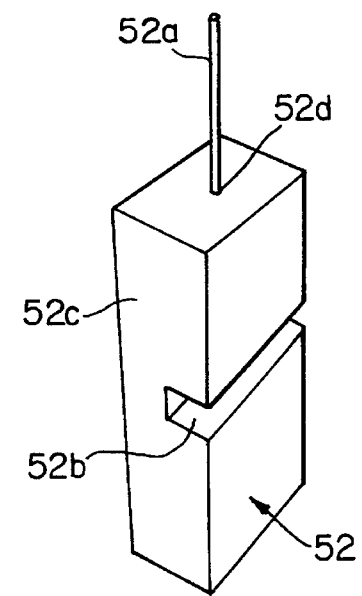
FIG. 8 is a perspective view of still another preferred composite material test specimen.

FIG. 8 depicts a rectangular specimen 52 which can be substituted for specimen 36. Test specimen 52 has a fiber 52a embedded within a matrix 52c forming a fiber-matrix interface 52d. Specimen 52 also includes a cut 52b.

In order to determine whether a test specimen is suitable for testing, a fluorescent dye can be applied to the test specimen. The dye flows into any cracks in the specimen making the cracks visible. Alternatively, a liquid containing radioactive isotopes can be applied to the test specimen. The cracks can then be detected by detecting concentrations of the isotopes.

Test specimens 36, 50 and 52 can be formed from a variety of materials including carbon fibers and ceramic matrices. Some other examples of the fiber/matrix materials are SIC/Epoxy, SIC/Fused Silica, SIC/Borosilicate glass and steel/cement. Virtually any specimen having a fiber embedded within a matrix that can be twisted within the matrix can be tested.

Figure 9:
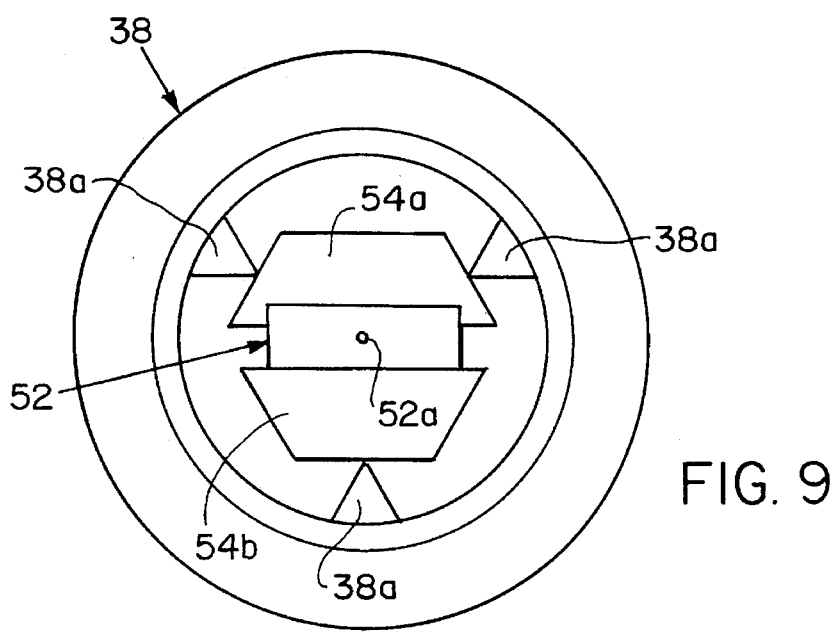
FIG. 9 is a top view of the rotatable chuck in which an adapter is employed to hold a rectangular test specimen.

In FIG. 9, when testing a rectangular specimen 52, an adapter is preferably employed to grip specimen 52. The adapter is preferably made of two halves of hex stock 54a and 54b and has angled surfaces for engaging jaws 38a.

Equivalents

While this invention has been particularly shown and described with references to preferred embodiments thereof, it will be understood by those skilled in the art that various changes in form and details may be made therein without departing from the spirit and scope of the invention as defined by the appended claims.

What is claimed is:

1. A method of measuring properties of a specimen of composite material, the specimen having a fiber extending through a matrix forming a fiber-matrix interface, a portion of the fiber extending from the matrix, the method comprising the steps of:

gripping the specimen of composite material with a first jaw;

gripping the fiber extending from the matrix with a second jaw;

rotating the fiber relative to the matrix; and measuring the torque transmitted through the fiber-matrix interface as the fiber is rotated relative to the matrix, the torque being measured with respect to angular rotation of the fiber relative to the matrix.

2. The method of claim 1 further comprising the steps of:

continuing rotation until the fiber debonds from the matrix; and measuring the torque transmitted through the fiber-matrix interface at the moment of debonding.

3. The method of claim 2 further comprising the step of sensing an acoustic report from the specimen with an acoustic transducer, the acoustic report resulting from the fiber debonding from the matrix during rotation.

4. The method of claim 1 in which the first jaw is coupled to a motor drive for rotating the fiber.

5. The method of claim 1 in which the second jaw is coupled to a torque transducer for measuring torque transmitted through the fiber-matrix interface to the fiber.

6. The method of claim 1 in which the motor drive comprises a stepper motor driven by electrical pulses coupled to a gear reducer, the gear reducer having a reduction ratio, and in which measuring the angular rotation of the fiber relative to the matrix comprises the steps of:

counting the number of electrical pulses used in driving the stepper motor;

correlating the number of electrical pulses into angular rotation of the stepper motor; and correlating the angular rotation of the stepper motor into angular rotation of the fiber relative to the matrix by accounting for the reduction ratio of the gear reducer.

7. The method of claim 1 further comprising the steps of:

sensing an acoustic report from the specimen with an acoustic transducer, the acoustic report resulting from an interface response caused by the fiber rotating relative to the matrix; and measuring the torque transmitted through the fiber-matrix interface at the moment of the acoustic report.

8. A method of measuring properties of a specimen of composite material, the specimen having a fiber extending through a matrix forming a fiber-matrix interface, a portion of the fiber extending from the matrix, the method comprising the steps of:

gripping the specimen of composite material with a first jaw;

gripping the fiber extending from the matrix with a second jaw;

rotating the fiber relative to the matrix with a motor drive coupled to the first jaw;

measuring the torque transmitted through the fiber-matrix interface to the fiber as the fiber is rotated relative to the matrix with a stationary torque transducer coupled to the second jaw, the torque being measured with respect to angular rotation of the fiber relative to the matrix;

sensing an acoustic report from the specimen with an acoustic transducer, the acoustic report resulting from an interface response caused by the fiber rotating relative to the matrix; and measuring the torque transmitted through the fiber-matrix interface at the moment of the acoustic report.

9. The method of claim 8 in which the motor drive comprises a stepper motor driven by electrical pulses coupled to a gear reducer, and in which measuring the angular rotation of the fiber relative to the matrix comprises the steps of:

counting the number of electrical pulses used in driving the stepper motor;

correlating the number of electrical pulses into angular rotation of the stepper motor; and correlating the angular rotation of the stepper motor into angular rotation of the fiber relative to the matrix by accounting for the reduction ratio of the gear reducer.

10. An apparatus for measuring properties of a specimen of composite material, the specimen having a fiber extending through a matrix forming a fiber-matrix interface, a portion of the fiber extending from the matrix, the apparatus comprising:

a first jaw for gripping the specimen;

a second jaw for gripping the fiber extending from the matrix;

a motor for rotating the fiber relative to the matrix; and a transducer for measuring torque transmitted through the fiber-matrix interface as the fiber is rotated relative to the matrix.

11. The apparatus of claim 10 further comprising an acoustic transducer for sensing an acoustic report from the specimen resulting from the fiber debonding from the matrix during rotation, the sensed acoustic report for signaling measurement of the torque transmitted through the fiber-matrix interface at the moment of the acoustic report.

12. The apparatus of claim 10 in which the motor comprises:

a stepper motor; and a gear reducer coupled to the stepper motor.

13. The apparatus of claim 12 further comprising a controller for controlling the rotation of the stepper motor.

14. The apparatus of claim 10 in which the first jaw is coupled to the motor.

15. The apparatus of claim 14 further comprising a three-axis slide adjustment coupled to the motor for adjusting the position of the motor.

16. The apparatus of claim 10 in which the second jaw is coupled to the transducer.

17. The apparatus of claim 8 further comprising an acoustic transducer for sensing an acoustic report from the specimen resulting from an interface response caused by the fiber rotating relative to the matrix, the sensed acoustic report for signaling measurement of the torque transmitted through the fiber-matrix interface at the moment of the acoustic report.

18. The method of claim 8 further comprising the step of continuing rotation until the fiber debonds from the matrix.

19. An apparatus for measuring properties of a specimen of composite material, the specimen having a fiber extending through a matrix forming a fiber-matrix interface, a portion of the fiber extending from the matrix, the apparatus comprising:

a first jaw for gripping the specimen;

a second jaw for gripping the fiber extending from the matrix;

a motor drive coupled to the first jaw for rotating the fiber relative to the matrix;

a stationary torque transducer coupled to the second jaw for measuring torque transmitted through the fiber-matrix interface as the fiber is rotated relative to the matrix; and an acoustic transducer for sensing an acoustic report from the specimen resulting from an interface response caused by the fiber rotating relative to the matrix, the sensed acoustic report for signaling measurement of the torque transmitted through the fiber-matrix interface at the moment of the acoustic report.

20. The apparatus of claim 19 in which the motor drive comprises:

a stepper motor; and a gear reducer coupled to the stepper motor.

21. The apparatus of claim 20 further comprising a controller for controlling the rotation of the stepper motor.

22. The apparatus of claim 19 further comprising a three-axis adjustment slide coupled to the motor drive for adjusting the position the motor drive.

\* \* \* \* \*